United States Patent [19]

Dhainaut et al.

[11] Patent Number: 5,919,801
[45] Date of Patent: Jul. 6, 1999

[54] N-SUBSTITUTED PIPERIDINES AS PDE4 INHIBITORS

[75] Inventors: Alain Dhainaut, Chatou; André Tizot, Verrieres le Buisson; Emmanuel Canet, Paris; Michel Lonchampt, Chevilly la Rue, all of France

[73] Assignee: Adir et Compagnie, Courbevoie, France

[21] Appl. No.: 08/934,409

[22] Filed: Sep. 19, 1997

[30] Foreign Application Priority Data

Sep. 20, 1996 [FR] France .................................. 96 11501

[51] Int. Cl.⁶ ...................... A61K 31/445; C07D 401/06
[52] U.S. Cl. .................. 514/326; 514/249; 514/311; 514/318; 514/330; 544/353; 546/152; 546/193; 546/210; 546/221
[58] Field of Search .............................. 544/353; 546/152, 546/193, 210, 221; 514/249, 311, 318, 330, 326

[56] References Cited

U.S. PATENT DOCUMENTS 5,434,158  7/1995  Shah ........................................ 514/278
5,459,151  10/1995  Lombardo ................................ 514/318

OTHER PUBLICATIONS

Burger "A guide to the chemical basis of drug design" Wiley Interscien Pub. p. 15, 1983.
Lowe et al. "Preparation of piperazine and piperidine derivatives . . . " CA 128:180426, 1998.

*Primary Examiner*—Ceila Chang
*Attorney, Agent, or Firm*—The Firm of Gordon W. Hueschen

[57] ABSTRACT

New N-substituted cyclic amines of formula:

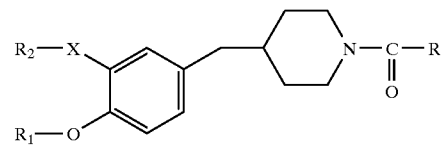

wherein: X, $R_1$, $R_2$ and R are as defined in the description, their optical and geometric isomers and physiologically tolerable salts thereof. The compounds of the invention are powerful PDE4 inhibitors and can be used therapeutically.

7 Claims, No Drawings

N-SUBSTITUTED PIPERIDINES AS PDE4 INHIBITORS

The present invention relates to new N-substituted cyclic amines and to pharmaceutical compositions containing them.

Those amines are inhibitors of group 4 phosphodiesterases and, for that reason, have especially valuable therapeutic applications.

In fact, the functions of most organic tissues are modulated by endogenous substances (hormones, neurotransmitters, autacoids) or by exogenous substances. For some of those substances, the biological effect is relayed at intracellular level by enzyme effectors, such as adenylate cyclase or guanylate cyclase. Stimulation of the enzymes that are responsible for the synthesis of cyclic nucleotides, such as cyclic adenosine-3', 5'-monophosphate (cAMP) and cyclic guanosine-3', 5'-monophosphate (cGMP), causes an increase in the intracellular level of those second messengers involved in regulating numerous biological functions (E. W. SUTHERLAND et T. W. RALL, Pharmacol. Rev., Vol. 12, p. 265,1960).

Breakdown of the cyclic nucleotides is effected by a family of enzymes, called phosphodiesterases (PDE), currently classified in 7 groups. The recognition of different isoforms within each of those groups, and of the tissue-specific or cell-specific distribution of certain isoforms, has stimulated research into increasingly specific inhibitors of individual types of isoenzyme (J. A. BEAVO, Physiological Rev., Vol. 75, no. 4, pp. 725–749, 1995). Of the various PDE families, PDE4 has been identified in a large number of tissues or cells, such as brain, heart, vascular endothelium, vascular and tracheobronchial smooth muscle and haematopoietic cells. Inhibition of the phosphodiesterases slows down the hydrolysis of the cyclic nucleotides and brings about an increase in cAMP and/or cGMP content.

PDE4 inhibitors, which are responsible for an increase in cAMP levels, have anti-inflammatory activities and relaxant effects on tracheobronchial smooth muscle, hence their therapeutic value in the field of respiratory pathology and pathologies associated with an inflammatory process (M. N. PALFREYMAN, Drugs of the Future, Vol. 20, no. 8, pp. 793–804, 1995; J. P. BARNES, Eur. Respir. J., Vol. 8, pp. 457–462, 1995; S. B. CHRISTENSEN and T. J. TORPHY, Annual Reports in Medicinal Chemistry, Vol. 29, pp. 185–194, 1994, Academic Press).

The present invention relates especially to the N-substituted cyclic amines of formula I:

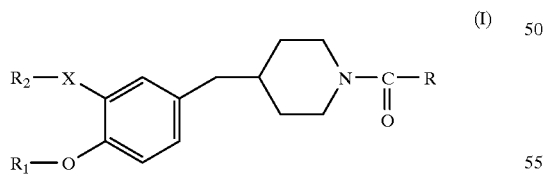

(I)

wherein:
X is selected from the group consisting of —CH=, —CH$_2$— and oxygen;
R$_1$ is selected from the group consisting of straight-chain and branched (C$_1$-C$_6$)alkyl that are unsubstituted, and substituted by one and more halogen (such as, for example, fluorine and chlorine);
R$_2$ is selected from the group consisting of:
a) saturated and unsaturated monocyclic hydrocarbon having from 3 to 6 carbon atoms inclusive and being unsubstituted, and substituted by one and more substituents selected from the group consisting of: halogen (such as, for example, fluorine and chlorine) and hydroxy;
b) polycyclic hydrocarbon, saturated (such as, for example, bicyclo[2,2,1]heptyl and adamantyl) and unsaturated, having from 7 to 10 carbon atoms inclusive and being unsubstituted, and substituted by one and more substituents selected from the group consisting of: halogen (such as, for example, fluorine and chlorine) and hydroxy;
c) saturated and unsaturated, straight-chain and branched (C$_1$-C$_{13}$)hydrocarbon that are unsubstituted, and substituted by one and more substituents selected from halogen (such as, for example, fluorine and chlorine) and hydroxy; and
d) (C$_1$-C$_{13}$)hydrocarbon defined in paragraph c) hereinabove, additionally substituted by one and more substituents selected from the group consisting of:
unsubstituted phenyl, and phenyl substituted by one and more substituents selected from the group consisting of halogen (such as, for example, fluorine and chlorine) and hydroxy;
saturated and unsaturated monocyclic hydrocarbon having from 3 to 6 carbon atoms inclusive and being unsubstituted, and substituted by one and more substituents selected from the group consisting of: halogen (such as, for example, fluorine and chlorine) and hydroxy; and
polycyclic hydrocarbon, saturated (such as, for example, bicyclo[2,2,1]heptyl and adamantyl) and unsaturated, having from 7 to 10 carbon atoms inclusive and being unsubstituted, and substituted by one and more substituents selected from the group consisting of: halogen (such as, for example, fluorine and chlorine) and hydroxy;
R is selected from the group consisting of phenyl, biphenylyl and naphthyl;
aromatic groups having 5 ring members and containing from 1 to 4 hetero atoms (identical and different), such as, for example, furyl, thienyl, pyrrolyl, imidazolyl, pyrazolyl, thiazolyl, isothiazolyl, oxazolyl, isoxazolyl, oxadiazolyl, triazolyl and tetrazolyl;
aromatic groups having 6 ring members and containing from 1 to 3 nitrogen atoms, such as, for example, pyridyl, pyrimidinyl, pyrazinyl, pyridazinyl and triazinyl;
saturated and unsaturated bicyclic aromatic groups having 9 and 10 carbon atoms and containing from 1 to 4 hetero atoms (identical and different), such as, for example, indolyl, indolinyl, benzofuranyl, benzothienyl, benzimidazolyl, benzopyranyl, benzopyrazolyl, benzotriazolyl, benzoxazolyl, benzisoxazolyl, chromanyl, chromenyl, quinolyl, dihydro- and tetrahydro-quinolyl, isoquinolyl, dihydro- and tetrahydro-isoquinolyl, quinazolinyl, quinoxalinyl, phthalazinyl, cinnolinyl, naphthyridinyl, pyridopyridyl, pteridinyl and purinyl;
the partially saturated bicyclic aromatic groups defined hereinabove, containing one and more carbonyl; and
each of the groups defined hereinabove for R, substituted by from 1 to 3 substituents selected from the group consisting of halogen R$_1$, CN, NO$_2$, OR$_3$, SR$_3$, COR$_3$, COOR$_3$, NR$_3$R$_4$, NCOR$_3$, CONR$_3$R$_4$ and SO$_2$NR$_3$R$_4$, with R$_3$ and R$_4$ which are identical or different, each representing hydrogen, and R$_1$ such as defined hereinabove.

The compounds of formula I may exist in the form of geometric isomers and/or of optical isomers, which, individually or in combination, also form part of the present invention.

Depending especially on the identity of R, some compounds of formula I may also be in the form of addition salts with pharmaceutically acceptable acids or bases, which physiologically tolerable salts are also included in the present invention.

The closest prior art to the present invention is illustrated especially by patent application WO 94/25437 A$_1$ which mentions N-acylated phenylpiperidines as bronchiodilatory and anti-inflammatory agents.

The present invention relates also to a process for the preparation of the compounds of formula I:
which is characterised in that:
a cyclic secondary amine of formula II:

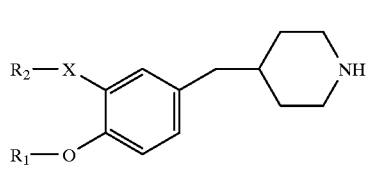

wherein: X, R$_1$, and R$_2$ are as defined hereinabove, is reacted with
a carbonyl compound of formula III:

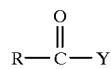

wherein:
R is as defined hereinabove and
Y is selected from the group consisting of hydroxy and chlorine.

When Y represents chlorine, it is especially advantageous to carry out the condensation according to known methods in the presence of a tertiary amine, such as triethylamine or 4-dimethylaminopyridine, or in the presence of a mineral base, such as sodium hydroxide, potassium hydroxide or sodium or potassium carbonate acting as acceptor for the hydracid formed, in a nonpolar aprotic solvent, such as dichloromethane, diethyl ether or tetrahydrofuran, or in a polar aprotic solvent, such as dimethylformamide, within a temperature range from 0 to 50° C., and keeping the reagents in contact for from 1 to 20 hours.

When Y represents hydroxy, it is advantageous to use peptide coupling methods (M. BODANSZKY and A. BODANSZKY, The Practice of Peptides Synthesis, Springer-Verlag, 1984) and, more especially, methods using dicyclohexylcarbodiimide (DCC) or a derivative thereof. The amide bond can also be formed in the presence of 2-(1H-benzotriazol-1-yl)-1,1,3,3-tetramethyluronium tetrafluoroborate (TBTU), to which there may be added an activator, such as hydroxybenzotriazole (HOBT) in accordance with described methods (M. S. BERNATOWICZ et al., Tetrahedron Lett., Vol. 30, p. 4645, 1989; A. G. BECK-SICKINGER, H. DURR and G. JUNG, Pept. Res., Vol. 4, p. 88,1991; G. E. REID and R. J. SIMPSON, Anal. Biochem., Vol. 200, p. 301, 1992; C. G. FIELS, D. H. LLOYD, R. L. MACDONNALD, K. M. OTTESON and R. L. NOBLE, Pept. Res., Vol. 4, p. 95, 1991), in a nonpolar aprotic solvent, such as diethyl ether, tetrahydrofuran or dichloromethane, within a temperature range from 0 to 50° C. depending on the solvent selected. It may also be especially advantageous to form the amide bond in the presence of propylphosphonic anhydride and of N-ethylmorpholine according to the method described by H. WISSMANN and H. J. KLEINER, Angew. Chem. Int. Ed., Vol. 19, pp. 133–134, 1980. When the method using propylphosphonic anhydride is selected, it is especially advantageous to use dimethylformamide as solvent, within a temperature range from 0 to 100° C. Depending on the acid and the method selected, the optimum contact time may vary from 1 to 20 hours within the temperature ranges defined hereinabove.

The starting materials of formula II are prepared by hydrolysis of the corresponding compounds of formula IV:

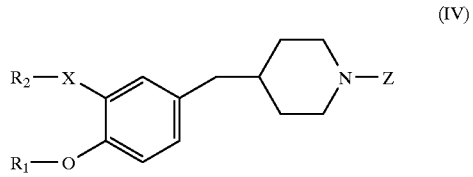

wherein:
X, R$_1$ and R$_2$ are as defined hereinabove, and
Z represents an acyl or alkoxycarbonyl group.

The compounds of formula IV may themselves be prepared according to the following reaction scheme in which, unless otherwise specified, X, R$_1$, R$_2$ and Z are as defined hereinabove:

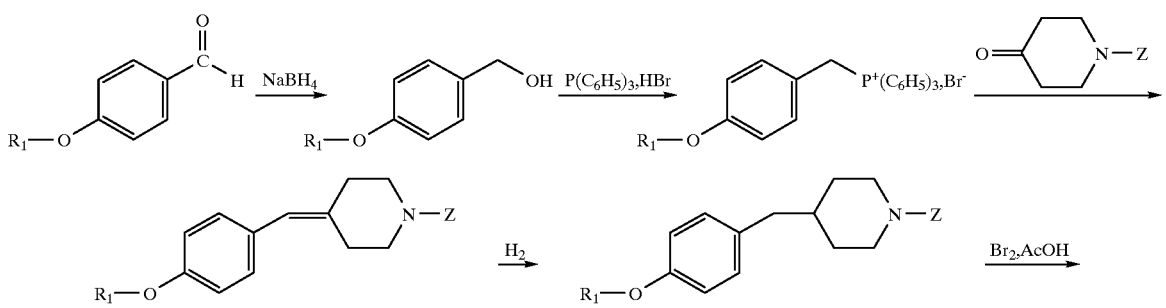

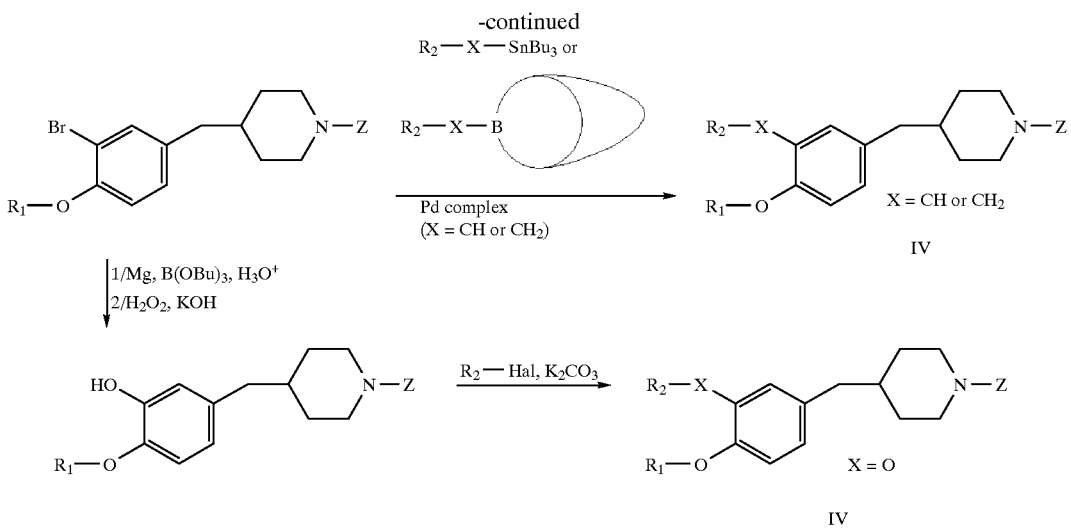

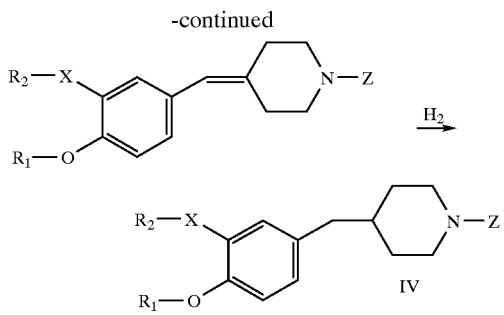

The substituted benzaldehydes used as starting materials in the above reaction scheme are commercial products or are synthesised by methods known to the person skilled in the art.

The methods used in the above reaction scheme of coupling bromobenzenes with organotin compounds:

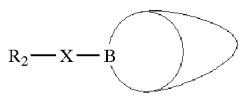

or with organoboron compounds:

in the presence of palladium complexes are known and are well described in the literature (J. K. STILLE, Angew. Chem. Int. Ed. Engl. 25, 508–524, 1986; N. MIYAURA and A. SUZUKI, Chem. Rev., Vol. 95, 2457–2483, 1995).

Moreover, in the case when, simultaneously, X represents an oxygen atom, $R_2$ does not contain any unsaturated bonds and $R_1$ and Z are as defined hereinabove, it is especially advantageous to proceed according to the following reaction scheme:

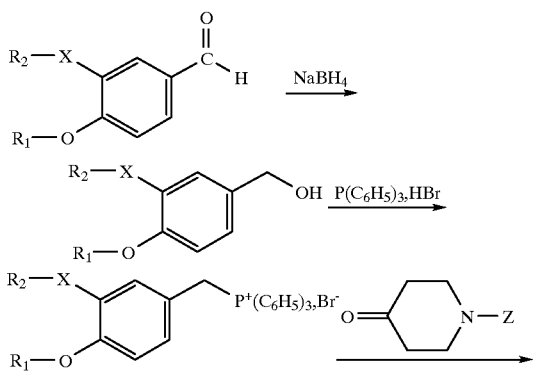

The substituted benzaldehydes used as starting materials in the latter scheme are synthesised using methods described in the literature (N. PALFREYMAN et al., J. Med. Chem., vol. 37, pp. 1696'1703, 1994).

The operating conditions used in the preceding two reaction schemes to obtain the ethylenic intermediates starting from phosphonium salts are the conditions conventionally described for a Wittig reaction.

The compounds of the present invention are very powerful inhibitors of group 4 phosphodiesterases and, for that reason, are especially valuable in therapeutic applications relating to inflammation and to bronchial relaxation and, more especially, in asthma and chronic obstructive bronchopathies (A. J. DUPLANTIER and J. B. CHENG, Annu. Rep. Med. Chem., vol. 29, p. 73–81, 1994), (C. D. NICHOLSON and M. SHAHID, Pulmonary Pharmacol., Vol. 7, p. 1–17, 1994), (T. J. TORPHY, G. P. LIVI and S. B. CHRISTENSEN, Drug News Perspect., Vol. 6, p. 203–214, 1993), (J. A. LOWE and J. B. CHENG, Drugs Future, Vol. 17, p. 799–807, 1992), and also in any disorders such as rhinites (I. RADERER, E. HAEN, C. SCHUDT and B. PRZYBILLA, Wien. Med. Wochenschr., Vol. 145, p. 456–458, 1995), acute respiratory distress syndrome (ARDS) (C. R. TURNER, K. M. ESSER and E. B. WHEELDON, Circulatory Shock, Vol. 39, p. 237–245, 1993), allergies and dermatites (J. M. HANIFIN and S. C. CHAN, J. Invest. Dermatol., Vol. 105, p. 84S–88S, 1995), (J. M. HANIFIN, J. Dermatol. Sci., Vol. 1, p. 1–6, 1990), psoriasis (E. TOUITOU, N. SHACO-EZRA, N. DAYAN, M. JUSHYNSKI, R. RAFAELOFF and R. AZOURY, J. Pharm. Sci., Vol. 81, p. 131–134, 1992), (F. LEVI-SCHAFFER and E. TOUITOU, Skin Pharmacol., Vol. 4, p.

286–290, 1991), rheumatoid arthritis (J. M. ANAYA and L. R. ESPINOZA, J. Rheumatol., Vol. 22, p. 595–599, 1995), autoimmune diseases (C. P. GENAIN et al. Proc. Natl. Acad. Sci., Vol. 92, p. 3601–3605, 1995), multiple sclerosis (N. SOMMER et al., Nat. Med., Vol. 1, p. 244–248, 1995), dyskinesias (T. KITATANI, S. HAYASHI and T. SAKAGUCHI, Nippon, Yakurigaku, Zasshi, Vol. 86, p. 353–358, 1985), glomerulonephritis (M. HECHT, M. MULLER, M. L. LOHMANN-MATTHES and A. EMMENDORFFER, J. Leukoc. Biol., Vol. 57, p. 242–249, 1995), osteoarthritis and septic shock (A. M. BADGER, D. L. OLIVERA and K. M. ESSER Circ. Shock, Vol. 44, p. 188–195, 1994; L. SEKUT et aL, Clin. Exp. Immunol., Vol.100, p.126–132,1995), AIDS (T. F. GRETEN, S. ENDRES et al., AIDS, Vol. 9, p. 1137–1144,1995), depression (N. A. SACCOMANO et al., J. Med. Chem., Vol. 34, p.291–298, 1991), and any neurodegenerative disease that is accompanied by inflammatory symptoms, such as Alzheimer's disease, Parkinson's disease, Huntington's disease, Down's syndrome and amyotrophic lateral sclerosis (G. Z. FEUERSTEIN et al., Ann. N.Y. Acad. Sci., Vol. 765, p. 62–71, 1995).

Those therapeutic indications are not limiting inasmuch as a decrease in the cellular cAMP concentration, whatever the cause and tissue location, results in cellular malfunction, giving rise to pathological symptoms, and may constitute an important therapeutic target for the products described.

The present invention relates also to pharmaceutical compositions comprising as active ingredient a compound of general formula I or a physiologically tolerable salt thereof, in admixture or association with an appropriate pharmaceutical excipient, such as, for example, distilled water, starch, talc, ethylcellulose, magnesium stearate or an appropriate solvent that allows the active ingredient to be inhaled in aerosol form.

The pharmaceutical compositions so obtained are generally in dosage form and may comprise from 1 to 500 mg of active ingredient, and may, for example, be in the form of tablets, dragees, gelatin capsules, suppositories, injectable or drinkable solutions or aerosols, and, depending on the case, may be administered by the oral, rectal, parenteral or local route.

The dosage may vary according to the age and weight of the patient, the route of administration, the nature of the disorder and associated treatments.

By way of example, the dosage by the oral route may range from 10 to 5000 mg of active ingredient daily.

The following Examples illustrate the present invention. Unless indicated otherwise, the melting points are determined using a capillary tube.

In the following synthesis procedures, all the starting materials used are either commercially available or are prepared according to processes described in the literature.

EXAMPLE 1

4-(3-Cyclopentyloxy-4-methoxybenzyl)-1-(imidazol-4-ylcarbonyl)piperidine

A solution containing 2.1 g of 4-(3-cyclopentyloxy-4-methoxybenzyl)piperidine, 2.6 g of 2-(1H-benzotriazol-1-yl)-1,1,3,3-tetramethyluronium tetrafluoroborate (TBTU), 1.1 g of N-hydroxybenzotriazole (HOBT), 1.6 ml of diisopropylethylamine and 1.0 g of 4-imidazole-carboxylic acid is stirred, under an argon atmosphere, at room temperature for 16 hours.

The reaction mixture is stirred for a few minutes with a saturated sodium carbonate solution. The organic phase is then taken up in water and subsequently dried over magnesium sulphate and concentrated. The residual oil is purified by flash chromatography using a $CH_2Cl_2$/ammoniacal $CH_3OH$ mixture (95:5) as elution system. 4-(3-Cyclopentyloxy-4-methoxybenzyl)-1-(imidazol-4-ylcarbonyl)piperidine taken up in ethanolic hydrogen chloride crystallises in the form of the hydrochloride, which melts at 204–207° C.

EXAMPLES 2 to 72

Starting with the appropriate starting materials, the compounds of the following Examples are prepared by proceeding as in Example 1:

2) 4-(3-cyclopentyloxy-4-methoxybenzyl)-1-(1-methylimidazol-4-ylcarbonyl)piperidine 3) 1-(5-aminoimidazol-4-ylcarbonyl)-4-(3-cyclopentyloxy-4-methoxybenzyl)piperidine 4) 4-(3-cyclopentyloxy-4-methoxybenzyl)-1-(2-methylimidazol-4-ylcarbonyl)piperidine 5) 1-(2-chloro-5-methylimidazol-4-ylcarbonyl)-4-(3-cyclopentyloxy-4-methoxybenzyl)-piperidie 6) 1-(2-chloro-1,5-dimethylimidazol-4-ylcarbonyl)-4-(3-cyclopentyloxy-4-methoxybenzyl)-piperidine 7) 4-(3-cyclopentyloxy-4-methoxybenzyl)-1-(4-fluorobenzimidazol-2-ylcarbonyl)piperidine 8) 4-(3-cyclopentyloxy-4-methoxybenzyl)-1-(5-piperidinocarbonylimidazol-4-ylcarbonyl)-piperidine 9) 4-(3-cyclopentylmethyl-4-methoxybenzyl)-1-(imidazol-4-ylcarbonyl)piperidine 10) 1-(imidazol-4-ylcarbonyl)-4-(4-methoxy-3-n-pentyloxybenzyl)piperidine 11) 1-(imidazol-4-ylcarbonyl)-4-(4-methoxy-3-n-pentylbenzyl)piperidine 12) 4-(3-allyloxy-4-methoxybenzyl)-1-(imidazol-4-ylcarbonyl)piperidine 13) 4-(3-allyl-4-methoxybenzyl)-1-(imidazol-4-ylcarbonyl)piperidine 14) (R,S)-4-[3-(2-exo-norborn-2-yloxy)-4-methoxybenzyl]-1-(imidazol-4-ylcarbonyl)piperidine 15) 4-(3-adamant-1-yloxy-4-methoxybenzyl-1-(imidazol-4-ylcarbonyl)piperidine 16) 4-(3-cyclopentyloxy-4-methoxybenzyl)-1-(pyrrol-2-ylcarbonyl)piperidine 17) 4-(3-cyclopentylmethyl-4-methoxybenzyl)-1-(pyrazol-4-ylcarbonyl)piperidine 18) 4-(3-cyclopentyloxy-4-methoxybenzyl)-1-(1-methylpyrazol-4-ylcarbonyl)piperidine 19) 4-(3-cyclopentyloxy-4-methoxybenzyl)-1-(5-methylisoxazol-3-ylcarbonyl)piperidine 20) 4-(3-cyclopentyloxy-4-methoxybenzyl)-1-(5-n-pentylisoxazol-3-ylcarbonyl)piperidine 21) 4-(3-cyclopentyloxy-4-methoxybenzyl)-1-(1,2,3-triazol-4-ylcarbonyl)piperidine 22) 4-(3-cyclopentyloxy-4-methoxybenzyl)-1-(1,2,4-triazol-3-ylcarbonyl)piperidine 23) 4-(3-cyclopentyloxy-4-methoxybenzyl)-1-(pyrazin-2-ylcarbonyl)piperidine 24) 4-(4-methoxy-3-n-pentylbenzyl)-1-(pyrazin-2-ylcarbonyl)piperidine 25) 1-(5-chloropyrazin-2-ylcarbonyl)-4-(3-cyclopentyloxy-4-methoxybenzyl)piperidine 26) 4-(3-cyclopentyloxy-4-methoxybenzyl)-1-(5-methylpyrazin-2-ylcarbonyl)piperidine 27) 1-(6-chloropyridazin-3-ylcarbonyl)-4-(3-cyclopentyloxy-4-methoxybenzyl)piperidine
28) 4-(3-cyclopentyloxy-4-methoxybenzyl)-1-(pyrimid-2-ylcarbonyl)piperidine
29) 4-(3-cyclopentyloxy-4-methoxybenzyl)-1-(quinol-4-ylcarbonyl)piperidine
30) 4-(3-cyclopentyloxy-4-methoxybenzyl)-1-(quinol-3-ylcarbonyl)piperidine
31) 4-(3-cyclopentyloxy-4-methoxybenzyl)-1-(quinol-5-ylcarbonyl)piperidine
32) 4-(3-cyclopentyloxy-4-methoxybenzyl)-1-(quinol-6-ylcarbonyl)piperidine
33) 4-(3-cyclopentyloxy-4-methoxybenzyl)-1-(quinol-8-ylcarbonyl)piperidine
34) 4-(3-cyclopentyloxy-4-methoxybenzyl)-1-(isoquinol-1-ylcarbonyl)piperidine
35) 4-(3-cyclopentyloxy-4-methoxybenzyl)-1-(isoquinol-3-ylcarbonyl)piperidine
36) 4-(3-cyclopentyloxy-4-methoxybenzyl)-1-(isoquinol-4-ylcarbonyl)piperidine
37) 4-(3-cyclopentyloxy-4-methoxybenzyl)-1-(quinoxalin-2-ylcarbonyl)piperidine
38) 4-(3-cyclopentylmethyl-4-methoxybenzyl)-1-(quinoxalin-2-ylcarbonyl)piperidine
39) 4-(4-methoxy-3-n-pentylbenzyl)-1-(quinoxalin-2-ylcarbonyl)piperidine
40) 4-(3-cyclopentyloxy-4-methoxybenzyl)-1-(quinoxalin-6-ylcarbonyl)piperidine
41) 4-(3-cyclopentyloxy-4-methoxybenzyl)-1-(indol-2-ylcarbonyl)piperidine
42) 4-(3-cyclopentyloxy-4-methoxybenzyl)-1-(5-fluoroindol-2-ylcarbonyl)piperidine
43) 4-(3-cyclopentyloxy-4-methoxybenzyl)-1-(indol-3-ylcarbonyl)piperidine
44) 4-(3-cyclopentyloxy-4-methoxybenzyl)-1-(1-methylindol-3-ylcarbonyl)piperidine
45) 4-(3-cyclopentyloxy-4-methoxybenzyl)-1-(indol-4-ylcarbonyl)piperidine
46) 4-(3-cyclopentyloxy-4-methoxybenzyl)-1-(indol-5-ylcarbonyl)piperidine
47) 1-(benzimidazol-5-ylcarbonyl)-4-(3-cyclopentyloxy-4-methoxybenzyl)piperidine
48) 1-(benzoxazol-5-ylcarbonyl)-4-(3-cyclopentyloxy-4-methoxybenzyl)piperidine
49) 4-(3-cyclopentyloxy-4-methoxybenzyl)-1-(cinnolin-4-ylcarbonyl)piperidine
50) 4-(3-cyclopentyloxy-4-methoxybenzyl)-1-(purin-6-ylcarbonyl)piperidine
51) 4-[4-(3-cyclopentyloxy-4-methoxybenzyl)piperidin-1-ylcarbonyl]-1-methylpyridinium iodide
52) 3-[4-(3-cyclopentyloxy-4-methoxybenzyl)piperidin-1-ylcarbonyl]-1-methylpyridinium iodide
53) (R,S)-4-[4-methoxy-3-(5-phenyl-2-pentyloxy)benzyl]-1-(imidazol-4-ylcarbonyl)piperidine hydrochloride
54) 4-[4-methoxy-3-(2-methyl-5-phenylpentyl)benzyl]-1-(imidazol-4-ylcarbonyl)piperidine
55) 4-(3-cyclopentyloxy-4-methoxybenzyl)-1-(4-dimethylaminophenylcarbonyl)piperidine
56) 1-(2-chloropyrid-4-ylcarbonyl)-4-(3-cyclopentyloxy-4-methoxybenzyl)piperidine
57) 4-(3-cyclopentyloxy-4-methoxybenzyl)-1-(4-methoxycarbonylbenzoyl)piperidine
58) 1-(4-carboxybenzoyl)-4-(3-cyclopentyloxy-4-methoxybenzyl)piperidine
59) 4-(3-cyclopentyloxy-4-methoxybenzyl)-1-(1,2,3-thiadiazol-4-ylcarbonyl)piperidine
60) 4-(3-cyclopentyloxy-4-methoxybenzyl)-1-(3-methylimidazol-4-ylcarbonyl)piperidine
61) 4-(3-cyclopentyloxy-4-methoxybenzyl)-1-(1,2,5-trimethylpyrrol-3-ylcarbonyl)piperidine
62) 4-(3-isopropoxy-4-methoxybenzyl)-1-(imidazol-4-ylcarbonyl)piperidine
63) 6-[4-(3-cyclopentyloxy-4-methoxybenzyl)piperidinocarbonyl]-1H-pyrimidine-2,4-dione
64) 5-[4-(3-cyclopentyloxy-4-methoxybenzyl)piperidinocarbonyl]-1H-pyrimidine-2,4-dione
65) 4-(3-butoxy-4-methoxybenzyl)-1-(1-methylimidazol-4-ylcarbonyl)piperidine
66) 4-(3-cyclopentyloxy-4-methoxybenzyl)-1-(1-isopropylimidazol-4-ylcarbonyl)piperidine
67) 4-(3-cyclopentyloxy-4-methoxybenzyl)-1-(quinol-2-ylcarbonyl)piperidine
68) 4-(3-cyclopentyloxy-4-methoxybenzyl)-1-(pyrazol-4-ylcarbonyl)piperidine
69) 4-(3-cyclopentyloxy-4-methoxybenzyl)-1-(2,6-dichlorobenzoyl)piperidine
70) 4-(3-cyclopentyloxy-4-methoxybenzyl)-1-(2,5-dimethylpyrrol-3-ylcarbonyl)piperidine
71) 1-(4-chlorobenzoyl)-4-(3-cyclopentyloxy-4-methoxybenzyl)piperidine
72) 4-(3-cyclopentyloxy-4-difluoromethoxybenzyl)-1-(3-methylimidazol-4-ylcarbonyl)-piperidine

EXAMPLE 73

4-(3-Cyclopentyloxy-4-methoxybenzyl)-1-(4-methoxybenzoyl)piperidine

A solution of 20 ml of tetrahydrofuran (THF) containing 1 g of 4-methoxybenzoyl chloride is added dropwise to a solution of 30 ml of THF containing 0.73 g of 4-(3-cyclopentyloxy-4-methoxybenzyl)piperidine, 0.78 ml of triethylamine and 0.2 g of 4-N,N-dimethylaminopyridine, and the mixture is stirred under argon at room temperature. The reaction mixture is stirred at room temperature for 4 hours, diluted with 150 ml of diethyl ether, washed with a saturated aqueous sodium carbonate solution and then with water, and washed with a 1N HCl solution and then washed again with water. The organic phase is dried over magnesium sulphate and concentrated. The residual oil is filtered over silica by the flash chromatography technique using a toluene/ethanol mixture (97:3) as eluant. 4-(3-Cyclopentyloxy-4-methoxybenzyl)-1-(4-methoxybenzoyl)piperidine is obtained in the form of an oil.

EXAMPLES 74–97

Starting with the appropriate starting materials, the compounds of the following Examples are prepared by proceeding as in Example 73:

74) 4-(3-cyclopentyloxy-4-methoxybenzyl)-1-(3,4-dimethoxybenzoyl)piperidine
75) 4-(3-cyclopentyloxy-4-methoxybenzyl)-1-(3,4,5-trimethoxybenzoyl)piperidine
76) 1-(4-acetoxybenzoyl)-4-(3-cyclopentyloxy-4-methoxybenzyl)piperidine
77) 1-(4-aminosulphonylbenzoyl)-4-(3-cyclopentyloxy-4-methoxybenzyl)piperidine 78) 4-(3-cyclopentyloxy-4-methoxybenzyl)-1-(4-trifluoromethylbenzoyl)piperidine
79) 4-(3-cyclopentyloxy-4-methoxybenzyl)-1-(2-nitrobenzoyl)piperidine
80) 4-(3-cyclopentyloxy-4-methoxybenzyl)-1-(3-nitrobenzoyl)piperidine
81) 4-(3-cyclopentyloxy-4-methoxybenzyl)-1-(4-nitrobenzoyl)piperidine
82) 4-(3-cyclopentyloxy-4-methoxybenzyl)-1-(thien-2-ylcarbonyl)piperidine
83) 4-(3-cyclopentyloxy-4-methoxybenzyl )-1-(furan-2-ylcarbonyl)piperidine
84) 4-(3-cyclopentyloxy-4-methoxybenzyl)-1-(furan-3-ylcarbonyl)piperidine
85) 4-(3-cyclopentyloxy-4-methoxybenzyl)-1-nicotinoylpiperidine
86) 1-(5-acetamidonicotinoyl)-4-(3-cyclopentyloxy-4-methoxybenzyl)piperidine
87) 1-(6-acetamidonicotinoyl)-4-(3-cyclopentyloxy-4-methoxybenzyl)piperidine
88) 4-(3-cyclopentyloxy-4-methoxybenzyl)-1-(6-hydroxynicotinoyl)piperidine
89) 4-(3-cyclopentyloxy-4-methoxybenzyl)-1-picolinoylpiperidine
90) 1-(2-chloro-6-methoxypyrid-4-ylcarbonyl)-4-(3-cyclopentyloxy-4-methoxybenzyl)-piperidine
91) 4-(3-cyclopentyloxy-4-methoxybenzyl)-1-isonicotinoylpiperidine
92) 1-(2-chloronicotinoyl)-4-(3-cyclopentyloxy-4-methoxybenzyl)piperidine
93)1-(6-chloronicotinoyl)-4-(3-cyclopentyloxy-4-methoxybenzyl)piperidine
94) 4-(3-cyclopentyloxy-4-methoxybenzyl)-1-(2,6-dichloroisonicotinoyl)piperidine
95) 1-(2-chloro-4-trifluoromethyinicotinoyl)-4-(3-cyclopentyloxy-4-methoxybenzyl)piperidine
96) 4-(3-cyclopentyloxy-4-methoxybenzyl)-1-(2,5-dichloronicotinoyl)piperidine
97) 1-(2-chloro-6-methylisonicotinoyl)-4-(3-cyclopentyloxy-4-methoxybenzyl)piperidine

EXAMPLE 98

PHARMACOLOGICAL STUDY

Measurement of PDE activity

U937 cells are cultivated in a culture medium (RPMI) containing 10% foetal calf serum. Briefly, the cells are lysed and then centrifuged (100,000 g, 60 min., 4° C.) and the supernatant is recovered in order to separate the different forms of PDE by HPLC (C. Lugnier and V. B. Schini, Biochem. Pharmacol., vol. 39 p.75–84, 1990).

The PDE activity is measured by the appearance of [$^3$H]5' AMP resulting from the hydrolysis of cyclic [$^3$H]AMP. The PDE and the cyclic [$^3$H]AMP (1 $\mu$Ci/ml) are incubated at 30° C. for 30 minutes. The radioactivity is measured using a liquid scintillation counter (Beckman LS 1701).

PDE 4 is characterised by:

hydrolysis of cyclic AMP the absence of inhibition by cyclic GMP of the hydrolysis of cyclic AMP inhibition by rolipram, the reference compound.

The compounds are studied at two concentrations ($10^{-7}$M and $10^{-5}$M), in duplicate. The results are expressed as % inhibition of the phosphodiesterase activity.

The compounds of the present invention demonstrate very significant inhibition of phosphodiesterase activity, which inhibition may, for example, exceed 80%, starting at a concentration of $10^{-7}$M.

We claim:
1. A compound selected from the group consisting of:
N-substituted cyclic amines of formula I:

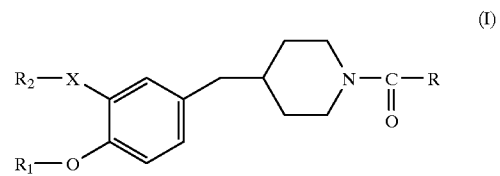

wherein:

X is selected from the group consisting of —CH=, —CH$_2$—, and oxygen;

R$_1$ is selected from the group consisting of straight-chain and branched (C$_1$–C$_6$)alkyl which are unsubstituted or substituted by one or more halogen;

R$_2$ is selected from the group consisting of:
a) saturated and unsaturated monocyclic hydrocarbons having 3 to 6 carbon atoms inclusive and being unsubstituted or substituted by one or more substituents selected from the group consisting of halogen and hydroxy;
b) saturated and unsaturated polycyclic hydrocarbons having 7 to 10 carbon atoms inclusive and being unsubstituted or substituted by one or more substituents selected from the group consisting of halogen and hydroxy;
c) saturated and unsaturated, straight-chain or branched (C$_1$–C$_{13}$)hydrocarbons which are unsubstituted or substituted by one or more substituents selected from the group consisting of halogen and hydroxy; and
d) (C$_1$–C$_{13}$)hydrocarbons as defined in paragraph c) hereinabove, additionally substituted by one or more substituents selected from the group consisting of:
unsubstituted phenyl and phenyl substituted by one or more substituents selected from the group consisting of halogen and hydroxy;
saturated and unsaturated monocyclic hydrocarbons having 3 to 6 carbon atoms inclusive and being unsubstituted or substituted by one or more substituents selected from the group consisting of halogen and hydroxy; and
saturated and unsaturated polycyclic hydrocarbons, having 7 to 10 carbon atoms inclusive and being unsubstituted or substituted by one or more substituents selected from the group consisting of halogen and hydroxy;

R is selected from the group consisting of
phenyl, biphenylyl, and naphthyl;
aromatic groups having 5 ring members and containing 1 to 4 hetero atoms which are identical or different,
aromatic groups having 6 ring members and containing 1 to 3 nitrogen atoms;
saturated and unsaturated bicyclic aromatic groups having 9 or 10 carbon atoms and containing 1 to 4 hetero atoms which are identical or different;
the partially saturated bicyclic aromatic groups defined hereinabove, containing one or more carbonyl; and each of the groups defined hereinabove for R, substituted by 1 to 3 substituents selected from the group consisting of halogen, $R_1$, CN, $NO_2$, $OR_3$, $SR_3$, $COR_3$, $COOR_3$, $NR_3R_4$, $NCOR_3$, $CONR_3R_4$ and $SO_2NR_3R_4$, with $R_3$ and $R_4$, which are identical or different, each representing hydrogen, and $R_1$ being as defined hereinabove;

their geometric isomers and their optical isomers, and addition salts thereof with a pharmaceutically-acceptable acid or base.

2. A compound of claim 1, which is 4-(3-cyclopentyloxy-4-methoxybenzyl)-1-(1-methylimidazol-4-ylcarbonyl)piperidine.

3. A compound of claim 1, which is 4-(3-cyclopentyloxy-4-methoxybenzyl)-1-nicotinoyl-piperidine.

4. A compound of claim 1, which is 4-(3-cyclopentyloxy-4-methoxybenzyl)-1-(quinol-4-ylcarbonyl)piperidine.

5. A compound of claim 1, which is 4-(3-cyclopentyloxy-4-methoxybenzyl)-1-(quinoxalin-2-ylcarbonyl)piperidine.

6. A method for treating a living animal body, afflicted with a respiratory pathology associated with an inflammatory process related to PDE4, comprising the step of administering to the said living animal body an amount of a compound of claim 1 which is effective for inhibition of PDE4 and alleviation of the said pathology.

7. A pharmaceutical composition which acts as an inhibitor of group 4 phosphodiesterases, and which can be used in the treatment of a respiratory pathology associated with an inflammatory process, comprising as active ingredient an effective amount of a compound according to claim 1, together with one or more pharmaceutical excipients.

* * * * *

UNITED STATES PATENT AND TRADEMARK OFFICE
CERTIFICATE OF CORRECTION

PATENT NO. : 5,919,801
DATED : July 6, 1999
INVENTOR(S) : A. Dhainaut, A. Tizot, E. Canet, M. Lonchampt It is certified that error appears in the above-identified patent and that said Letters Patent is hereby corrected as shown below:

Column 6, line 39: "1696'1703, 1994)." should read
-- 1696-1703, 1994).--.

Column 8, line 22: "piperidie" at the end of the line
should read -- piperidine --.

Column 11, line 38: "trifluoromethyinicotinoyl)"
should read -- trifluoromethylnicotinoyl) --.

Signed and Sealed this

Twenty-eighth Day of March, 2000

Attest:

Q. TODD DICKINSON

Attesting Officer   Commissioner of Patents and Trademarks